United States Patent
Ostermeyer

(10) Patent No.: US 9,683,929 B2
(45) Date of Patent: Jun. 20, 2017

(54) OPTICAL MEASURING SYSTEM FOR MEASURING OPTICAL POLARIZATION PROPERTIES OF A SAMPLE

(71) Applicant: Anton Paar GmbH, Graz (AT)

(72) Inventor: Martin Ostermeyer, Gehrden bei Hannover (DE)

(73) Assignee: Anton Paar GmbH, Graz (AT)

( * ) Notice: Subject to any disclaimer, the term of this patent is extended or adjusted under 35 U.S.C. 154(b) by 0 days.

(21) Appl. No.: 14/668,880

(22) Filed: Mar. 25, 2015

(65) Prior Publication Data

US 2015/0276581 A1    Oct. 1, 2015

(30) Foreign Application Priority Data

Mar. 26, 2014   (DE) .................. 10 2014 104 268

(51) Int. Cl.
*G01J 4/00*     (2006.01)
*G01N 21/21*    (2006.01)
(Continued)

(52) U.S. Cl.
CPC ............ *G01N 21/21* (2013.01); *G01N 21/01* (2013.01); *G01N 21/0332* (2013.01);
(Continued)

(58) Field of Classification Search
CPC ... G01N 2021/0106; G01N 2021/0367; G01N 21/01; G01N 21/0332; G01N 21/05; G01N 21/21; G01N 2201/061; G01N 2201/0683
(Continued)

(56) References Cited

U.S. PATENT DOCUMENTS 2,666,355 A    1/1954  Turnit
4,988,199 A    1/1991  Paul
(Continued)

FOREIGN PATENT DOCUMENTS

EP           0902270 B1    4/2005
WO    WO 2006052644 A2    5/2006

OTHER PUBLICATIONS

Cotterman, Bruce W.; Instructional Polariscope, United States Statutory Invention Registration H76, Jul. 1, 1986, United States Patent Office, Washington, D.C., U.S.A.

*Primary Examiner* — Sunghee Y Gray
(74) *Attorney, Agent, or Firm* — Robert A. Blaha; Smith Tempel Blaha LLC

(57) ABSTRACT

An optical measuring system measures polarization optical properties of a sample. The system includes (a) a light source that emits measuring light along an optical axis of an analysis beam path, (b) a polarization state generator, arranged downstream with respect to the light source in the analysis beam path which provides light with a defined polarization state, (c) a sample holder, arranged downstream with respect to the polarization state generator in the analysis beam path which accommodates the sample, (d) a polarization state analyzer, arranged downstream with respect to the sample holder in the analysis beam path which measures the polarization state of the measuring light after passing through the sample, and (e) a mechanical support structure, at which at least the polarization state generator, the sample holder and the polarization state analyzer are directly attached. Also described is a method for producing such an optical measuring system.

24 Claims, 4 Drawing Sheets

(51) Int. Cl.
  *G01N 21/01* (2006.01)
  *G01N 21/03* (2006.01)
  *G01N 21/05* (2006.01)
(52) U.S. Cl.
  CPC ..... *G01N 21/05* (2013.01); *G01N 2021/0106* (2013.01); *G01N 2021/0367* (2013.01); *G01N 2201/061* (2013.01); *G01N 2201/0683* (2013.01)
(58) Field of Classification Search
  USPC .......................................................... 356/367
  See application file for complete search history.

(56) References Cited

U.S. PATENT DOCUMENTS

| | | | | |
|---|---|---|---|---|
| 5,636,017 A | * | 6/1997 | Bruno | G01N 21/05 356/246 |
| 6,643,021 B1 | | 11/2003 | Kawamura | |
| 7,952,711 B1 | * | 5/2011 | Chen | G01N 21/23 356/364 |
| 2005/0270534 A1 | * | 12/2005 | Rising | G01N 21/0332 356/432 |
| 2007/0263207 A1 | * | 11/2007 | Mertz | G01N 21/0332 356/300 |
| 2009/0324448 A1 | * | 12/2009 | Yano | G01N 1/4077 422/82.05 |
| 2013/0265584 A1 | * | 10/2013 | Babic | G01B 9/02055 356/491 |

* cited by examiner

OPTICAL MEASURING SYSTEM FOR MEASURING OPTICAL POLARIZATION PROPERTIES OF A SAMPLE

CROSS-REFERENCE TO RELATED APPLICATION

This application claims the benefit of the filing date of the German Patent Application No. 10 2014 104 268.9, filed 26 Mar. 2014, the disclosure of which is hereby incorporated herein by reference.

TECHNICAL FIELD

Embodiments of the present invention relate to an optical measuring system for measuring optical polarization properties of a sample, more particularly of a liquid sample.

BACKGROUND

Measuring systems designed as a polarimeter can measure different optical polarization properties of a sample. In the simplest case the changes in the oscillation plane of linearly polarized light, known as optical rotation and caused by the optical activity of the sample, is measured. However, also further optical polarization properties of the sample can be measured, right up to a full determination of the so-called Müller matrix, which is the transformation matrix for the Stokes vector. As is known, the Stokes vector describes the polarization state of an electromagnetic wave. The Müller matrix characterizes the sample in question in terms of its interaction with the electromagnetic wave. More particularly, the Müller matrix describes the change in the polarization state of an electromagnetic wave, for example with a reflection at a sample boundary or with a transmission of the electromagnetic wave through the sample.

A polarimeter for measuring the optical polarization properties of a sample comprises a mechanical support structure on which the components of relevance for measuring are mounted by means of suitable holders. These components comprise a light source, which emits collimated measuring light along an optical axis of the polarimeter. For producing the collimated light, diaphragms and/or lenses can be used. The measuring light passes through a polarization state generator (PSG) which produces a defined polarization state of the measuring light. The measuring light then penetrates through the sample to be examined. In the case of a liquid sample this is situated in a cuvette. The polarization state of the measuring light is changed with passing through the sample and is detected by means of a polarization state analyzer (PSA).

In order to achieve a measuring accuracy, the mechanical stability of the structure of a polarimeter is subject to the highest requirements. More particularly, torsions between the precision-determining elements PSG and PSA must be avoided. This can be achieved by a correspondingly solid mechanical support structure on which there are mounted components that determine the measuring accuracy of the polarimeter. A solidly designed support structure results in the polarimeter not only being particularly heavy but also having relative large structural dimensions.

There may be a need for optimizing the structure of an optical measuring system so that it can be simply produced in a compact design.

SUMMARY OF THE INVENTION

This need may be met by the subject matters of the independent claims. Advantageous forms of embodiments of the present invention are described in the dependent claims.

In accordance with a first aspect of the invention an optical measuring system for measuring optical polarization properties of a sample is described. The optical measuring system comprises (a) a light source, adapting for emitting measuring light along an optical axis of an analysis beam path of the optical measuring system, (b) a polarization state generator, which is arranged downstream of the light source in the analysis beam path and which is configured to provide the measuring light with a defined polarization, (c) a sample holder, which is arranged downstream with respect to the polarization state generator in the analysis beam and which is designed to hold the sample to be measured, (d) a polarization stage analyzer, which is arranged downstream with respect to the sample holder in the analysis beam path and which is configured to measure the polarization state of the measuring light after passing through the sample, and (e) a mechanical support structure at which at least the polarization state generator, the sample holder and the polarization state analyzer are directly attached.

The described optical measuring system is based on the idea that by means of a direct arrangement and fastening of at least some components, more particularly optical components, at the mechanical support structure, an optical measuring system in the form of a polarimeter can be produced in a particularly compact design. Descriptively expressed, at least a majority of the sensor technology required for the polarimeter as well as the sample to be analyzed can be located on the mechanical support structure. As a result, the mechanical stability of the entire optical measuring system is improved in a simple manner and the susceptibility to vibration and especially the susceptibility to torsion can be reduced with a lighter construction. More particularly, a high susceptibility to relative torsion between the polarization state generator (PSG) and the polarization state analyzer (PSA) would lead to a considerable deterioration in the measuring accuracy.

In this document, the term "measuring light" is taken to mean any type of electromagnetic radiation which can interact with an optical polarization sample in such a way that on passing through the sample the polarization of the electromagnetic radiation is altered. The measuring light can comprise largely mono-chromatic radiation or broad-band radiation with different wavelengths. The measuring light can comprise radiation in any visible and non-visible spectral ranges. Preferred is measuring light visible to the human eye. However, the measuring light can also be infrared or ultraviolet measuring light. The nature of the used optical components of the described optical measuring system should of course be matched to the spectrum of the measuring light. The terms "optic" or "optical" should therefore be broadly interpreted in this document and are not restricted to the spectral range visible to the human eye.

In this document the term "downstream" is to be understood as the direction along the optical axis of the analysis beam path, along which direction the measuring light in the optical measuring system propagates.

The term mechanical support structure can be taken to mean any physically formed basic element that has the required mechanical stability to hold the components in question in a precisely defined relative spatial position in relation to each other. The mechanical support structure can consist of a solid component, for example a solid (metallic) plate, or can comprise such a solid component. Alternatively, or in combination, the mechanical support structure can also have a framework structure with as high mechanical stability as possible. Such framework structures are used, for example, for optical experiments, in the case of which a plurality of optical components are fixed, for example by means of predrilled threaded holes, and can be fixed in a simple manner by means of loosening a corresponding screw connection in another position at the surface of the framework structure.

Since the mechanical support structure in accordance with embodiments of the invention holds optical components of the optical measuring system, it can also be designated as a so-called optical bank. Due to the direct arrangement of the optical components of the optical measuring system at the optical bank, in this document the mechanical support structure is also called an integrated optical bank (JOB).

In this document "directly attached" can indicate in particular that the relevant component is attached to the mechanical support structure without a stand structure which keeps the relevant component at a distance from (the surface of) the mechanical support structure. However, it is pointed out that the respective component may also have a housing. In this case it is not the optical element of the optical component itself that is directly fastened to the mechanical support structure, but the housing of the respective component.

It is pointed out that not all components have to be mounted at the mechanical support structure. It is sufficient if those components are mounted on the mechanical support structure in which the mounting stability determines the measuring accuracy of the optical measuring system. For example, the light source can comprise a light-generating element, for example a laser or a light diode, and an optical fiber, wherein the light-generating element, possibly including wavelength-selective elements, can be mounted elsewhere and the measuring light generated by the light-emitting element can be introduced into the analysis beam path of the optical measuring system by way of the optical fiber.

It is further pointed out that the light source and the PSG can also be realized by means of a common optical component. Such a common optical component can for example be a laser, which already emits linearly polarized laser light that constitutes the measuring light with the defined polarization state.

The PSA can also be composed of several optical or optoelectronic components. More particularly, the polarization state analyzer can comprise a light detector and an optical element, which only lets light with a defined polarization hit the light detector.

In accordance with an example of embodiment of the invention, the optical measuring system also has a housing, which surrounds at least the polarization state generator and the polarization state analyzer, wherein the sample holder is located outside from the housing.

The arrangement of the sample holder outside from the housing may have the advantage that the sample to be measured can easily be replaced with another sample to be measured in a following measuring procedure. At the same time the central optical components of the described optical measuring system, the PSG and the PSA, which are typically very sensitive components of the optical measuring system, are protected by the housing against undesirable external influences.

The sample holder can in particular be located at an outer wall of the housing so that the described optical measuring system can still be realized in a particularly compact design.

In order to realize the direct arrangement of the sample holder at the mechanical support structure in accordance with embodiments of the invention, the housing can have an interruption in the region of the sample holder, and/or the surface of the mechanical support can constitute a part of the housing in the region of the sample holder.

By way of the described housing the entire optical measuring system, but in particular the optical components of the measuring system, can be protected against a formed condensation. In this respect the inside of the housing can be separated from the environment in a gas-impermeable manner. Because of the aforementioned compact design of the entire optical measuring system this gas-impermeable separation can be achieved in a very simply manner. Alternatively or in combination, the interior of the housing can also be filled respectively flushed with dry air or a protective gas.

In accordance with a further example of embodiment of the invention, the sample holder can be designed to hold a cuvette and, more particularly, to hold a throughflow cuvette. With this, the described optical measuring system can also be advantageously used for measuring fluid samples. As in practice this is the most common application for polarimeters, the described optical measuring system can be used for a large number applications in the field of optical analysis.

Preferably the cuvette is arranged in such a manner that the inlet and outlet windows of the cuvette are oriented perpendicularly to the beam of the measuring light. This requirement can be automatically fulfilled with the described optical measuring system as due to the direct application of the sample holder at the mechanical support structure, in the case of normally spatially firm (but detachable) fixation of the cuvette in respectively at the sample holder, the cuvette is connected to the optical support structure in a precisely defined relative spatial position.

The sample holder should be designed in such a way that when replacing the cuvette the new cuvette is reproducibly placed in the correct spatial position.

The sample holder and/or the above-described housing of the optical measuring system can be designed in such a way that the sample holder area is sealed with regard to the interior of the optical measuring system. This can prevent the interior of the optical measuring system from becoming contaminated with the fluid sample in the event of accidental spillage or leakage of the fluid from the cuvette. This applies in particular to connections or ducts via which a fluid sample to be measured while it is flowing through is introduced and removed again.

In accordance with a further example of embodiment of the invention the sample holder is realized by a recess which is formed in the mechanical support structure. This means that the mechanical support structure at least partially adopts the function of a sample chamber enclosure. In the case of the optical polarization measurement of a fluid sample and an accidental spilling of the sample fluid, the spilled fluid will be collected in the recess, which can also be designated as a cavity, and can then be easily removed, for example by simple wiping away. This facilitates any required cleaning of the optical measuring system.

In accordance with a further example of embodiment of the invention the optical measuring system also has a temperature control device, which is attached to the mechanical support structure in such a way that the temperature of a sample being located in the sample holder can be indirectly controlled by means of the mechanical support structure.

The described temperature control device also allows the optical measuring system to be used for optical polarization measurements where the optical polarization properties of the samples depend on the temperature. As for most samples no temperatures corrections have been established, for comparative measurement these samples have to be adjusted to a defined measuring temperature. In pharmacopoeias a temperature of, for example, 20° C. or 25° C. is often stipulated for optical polarization measurements.

It is pointed out that the arrangement of the temperature control device described here at the mechanical support structure is a completely new approach for controlling the temperature of the sample to be measured. In known polarimeters, with which the temperature of the sample to be measured can be controlled, it is normally attempted to exclude the mechanical support structure, to which the optical components of the polarimeter are directly or indirectly attached by means of suitable holders, from a temperature control and instead to adjust the temperature of the sample to be measured as directly as possible.

In accordance with a further example of embodiment of the invention the temperature control device is attached to one side of the mechanical support structure and the sample holder is attached to a second side of the mechanical support structure, wherein the first side is opposite the second side. In relation to the sample holder, the temperature control device is thus on an opposite side of the mechanical support structure. In this way the distance between the temperature control device and the sample to be measured and the corresponding thermal conduction path can be kept short. This makes possible a rapid temperature control of the sample to be measured.

By means of the arrangement of the temperature control device and the sample holder at opposite sides of the mechanical support structure allows a temperature control of the sample that requires relatively little structural space and can therefore be implemented in a cost-effectively manner.

In accordance with a further example of embodiment of the invention the temperature control device is a thermoelectric temperature control device which comprises one thermoelectric element or several thermoelectric elements. Temperature control of the sample to be measured is therefore possible solely by means of a suitable electrical connection of the thermoelectric temperature control device to a voltage supply respectively to a current supply.

The temperature control device can be attached to the mechanical support structure by means of a thermally conductive adhesive and/or a heat-conducting paste. Other thermotransfer materials, e.g. graphite or silicone films, can also be used.

It is pointed out that thermoelectric elements can only be efficiently temperature controlled if an efficient cooling element can dissipate the heat produced by them to the surrounding. The cooling element can be realized by means of an external cooling with a cooling fluid. This can take place in a known manner by means of connections for a cooling fluid, for example water, or a cooling fluid including a thermostat. In a particularly simple embodiment, forced ventilation of the cooling element by means of fans, for example, can be used. Depending on whether the cooling element is located inside the housing of the optical measuring system or outside the housing of the optical measuring system, the cool air flow must be directed between the mechanical support structure and the cooling element at least partially inside or outside of the housing.

It is pointed out that a cooling fluid flow of the temperature control devices should if possible be kept away from the components of the optical measuring system and, more particularly, the sample to be measured, in order not to make the temperature control of the relevant components unnecessarily difficult.

In accordance with a further example of embodiment of the invention the at least one thermoelectric element is clamped between a cooling element of the thermoelectric temperature control device and the mechanical support structure. This may have the advantage that a good thermal connection of the thermoelectric temperature control device to the mechanical support structure can be achieved in a structurally particularly simple manner.

In accordance with a further example of embodiment of the invention the support structure and the at least one thermoelectric element are coupled to each other in an almost torsion-free manner.

Freedom from torsion or at least "torsion paucity" between the support structure and the at least one thermoelectric element can be realized in many different ways. A person skilled in the art with structural abilities will have no problem in creating a suitable mechanically almost torsion-free connection, depending on the basic design of the optical measuring system. However, in connection with this it should be mentioned that the at least almost torsion-free connection is preferably implemented in such a way that there is a good thermal coupling between at least one part of the mechanical structure and the at least one thermoelectric element.

In accordance with a further example of embodiment of the invention the optical measuring system further comprises a temperature regulation circuit for a regulated temperature controlling of a sample accommodated in the sample holder. Such a temperature regulation circuit can for example be realized in that a temperature sensor is applied to the sample holder and the temperature control device is operated so that this temperature sensor measures a predetermined temperature. In the case of a fluid sample contained in a cuvette, the temperature sensor can be applied to a holder for the cuvette. In connection with this it is assumed that at least when the temperature sensor delivers a constant measuring signal corresponding to the predetermined temperature for a predefined period of time, the temperature of the sample has adjusted to the predetermined temperature of the temperature sensor.

In an embodiment improved in terms of the precision of the temperature regulation, the temperature of the cuvette can be measured by a temperature sensor mounted therein and the control circuit implemented so that temperature of the cuvette is directly regulated.

In accordance with a further example of embodiment of the invention the support structure is designed in several parts and has a first support element and a second support element as well as a coupling mechanism which connects the two support element in an at least mechanically torsion-free manner.

The two support elements can spaced at a distance from one another by means of at least one void or at least one gap, the coupling mechanism can be located within the at least one void or the at least one gap.

The coupling mechanism can be implemented by a person skilled in the art in various ways. For example a connection construction can be used as it is common with optical mirror holders. Thereby, the elements to be connected are pulled towards each other by means of springs. Between the elements to be connected there are placed three spheres which act as spaces and constitute the contact points. By means of the use of spheres and springs, the surfaces via which both support elements are in contact with each other are particularly small, which results in a very poor thermal contact. At the same time such connection structures allow for a mechanically stable and thereby in particular a torsion-free connection between both support elements.

It is pointed out that for a high measuring accuracy it may be of advantage if the thermal coupling between the different support elements is as good as possible so that the entire optical measuring system is uniformly temperature-controlled. For this reason the described (mechanical) coupling mechanism can also be combined with a thermal coupling mechanism, which particularly by means of a high thermal output ensures that all support elements of the support structure are at least approximately uniformly temperature-controlled.

Another assembly possibility for connecting the two support element consists in the creation of combinations of grooves and depressions in a surface in combination with spheres and screws. Spring elements can also be used for the coupling mechanism.

In accordance with a further example of embodiment of the invention the polarization state generator is arranged at the first support element and the polarization state analyzer is arranged at the second support element. This can mean that in at least one section both support elements are in a direction parallel to the optical axis of the analysis beam at a distance form one another.

By means of attaching the PSG and PSA at different support elements of the mechanical support structure the two central optical components of the optical measuring system are coupled to each other in a mechanically stable manner. Depending on the use and/or the design of a thermal coupling element the PSG can be coupled to the PSA to a thermally greater or lesser extent.

In accordance with a further example of embodiment of the invention the support structure also comprises a third support element at which the sample holder is arranged, and the coupling mechanism comprises a first coupling structure and a second coupling structure, wherein the first coupling structure is arranged between the first support element and the third support element and the second coupling structure is arranged between the third support element and the second support element.

As in accordance with the basic principle of a polarimeter the sample to be measured must be located between the polarization state generator and the polarization state analyzer, the third support element is arranged between the first support element and the second support element.

The described use of a third support element which is assigned to the sample holder, and thus the sample to be measured, may have the advantage that controlling the temperature of the sample does not necessarily also have to result in a change in the temperature of the central optical components PSG and PSA. This takes on particular importance if the above-described temperature control device for controlling the temperature of the sample to be measured is used and attached to the third support element. The temperature control device can thus be operated in terms of optimum temperature regulation without any pre-determined, limiting operating temperatures, particularly of the PSG and/or the PSA having to be taken into account.

The described construction of the mechanical support structure, which comprises at least three support elements being thermally separated from one another, may also be of great advantages if the required sample temperature range is greater than the admissible temperature for components of the optical measuring system, more particularly for the PSG and/or PSA.

The construction described here may also be of advantage if at least parts of the mechanical support structure should not be temperature-controlled and/or the temperature of the sample is directly controlled, more particularly cooled, by a known temperature control device.

It is pointed out that the coupling mechanism can also ensure that mechanical stresses, which occur in a support element, for example, are not transmitted to the other support element. Such mechanical stresses can be produced by the temperature control device, for example, and can be transmitted to the mechanical support structure. In connection with this it is clearly evident that such transmitted mechanical stresses could also result in undesirable torsions between the PSG and the PSA. In such an event the measuring accuracy of the polarimeter would be reduced accordingly.

A further advantage of the described segmentation of the mechanical support structure may be that the thermal mass of only the third support element is considerably less than the thermal mass of the entire mechanical support structure. As for the thermal stabilization of the sample to be measured only the thermal mass of the (third) support element, at which the sample holder is located, is of relevance, this form of embodiment of the described optical measuring system allows for particularly rapid temperature changes/temperature adjustments of the sample to be measured.

In order to bring about stable measuring conditions as rapidly as possible, those segments of the support structure which bear the components PSG or PSA can be separately temperature-controlled. Thereby, as needed these components can be brought at a temperature being different to the temperature of the sample to be measured. This can be done, for example, by a separate temperature control being used for the components PSA and/or PSA.

It is pointed out that also in this form of embodiment, depending on the special application, it can be useful if the thermal coupling between (a) the third support element and (b) the first and/or the second support element is particularly good, as in this case the entire optical measuring system is automatically uniformly temperature-controlled and after setting a changed temperature it is only necessary to wait for a certain time until all the components are in thermal equilibrium.

In accordance with a further example of embodiment of the invention the two support elements are arranged at a distance from each other in a direction perpendicular to the optical axis of the analysis beam path.

The first support element can, for example, be arranged above the second support element support element, wherein a least some of the optical components of the described optical measuring system as well as the sample holder can be arranged at the upper side of the first support element. At the underside of the second support element the above-described temperature control device can be attached, which thus initially temperature controls the second (lower) support element. Temperature controlling of the sample to be measured thus takes place indirectly via temperature controlling of the second (upper) support element. As the coupling mechanism described above only permits only a relatively small heat conduction due to the relatively small mechanical contact points, the thermal coupling between the two support elements can also take place by means of heat radiation. For this it may be of particular advantage if the two support elements each have a flat outer side, wherein the two outer sides face each other and are only separated by the above-described coupling mechanism and are thus arranged at a small distance from one another.

It is pointed out that thermal coupling solely by means of heat radiation can be very weak, which during the operation of the optical measuring system can result is extremely long periods of time to carry out temperature control. However, the thermal coupling between the second (lower) support element and the first (upper) support can be relatively simply improved in that instead of air, a fluid with a particularly good conductivity is filled into the (as narrow as possible) gap between the two support elements (and is prevented from draining out). In this case a "floating" bearing is obtained which can also provide good torsion coupling. Instead of a thermally conductive fluid a soft thermo-transfer layer can also be inserted in the gap between the two supporting elements. However, in this case the ratio between the contact surface of at least one of the two support elements and the gap width should not be too large, as otherwise transmission of torsion can occur again.

In accordance with a further aspect of the invention a method for producing an optical measuring system for measuring optical polarization properties of a sample is described. The optical measuring system can be a measuring system as has been described above. The described production method comprises (a) providing a mechanical support structure, (b) providing a light source, adapted for emitting measuring light along an optical axis of an analysis beam path of the optical measuring system, (c) attaching, directly at the mechanical support structure, a polarization state generator downstream with respect to the light source in the analysis beam path, whereby the polarization state generator is configured to provide the measuring light with a defined polarization state, (d) attaching or forming, directly at the mechanical support structure, a sample holder downstream of the polarization state generator in the analysis beam path, wherein the sample holder is designed to accommodate the sample to the measured, (e) attaching, directly at the mechanical support structure, a polarization state analyzer downstream with respect to the sample holder in the analysis beam path, wherein the polarization state analyzer is configured to measure the polarization state of the measuring light after passing through the sample.

The described production method is also based on the idea that by means of a direct arrangement and fastening of at least some components, more particularly optical components, at the mechanical support structure, an optical measuring system designed as a polarimeter can be realized in an in particular compact construction.

It is pointed out that forms of embodiment of the invention have been described with reference to different subject matters of the invention. More particularly, some forms of embodiment of the invention have been described with device claims and other forms of embodiment of the invention have been described with method claims. However, on reading this application it will be immediately clear to a person skilled in the art that, unless explicitly stated otherwise, in addition to a combination of features belonging to one type of subject matter, any combination of features belonging to different types of subject matter is possible.

Further advantages and features of embodiments of the present invention result from the following exemplary description of currently preferred forms of embodiment. The individual figures of the drawing of this application should only been seen as schematic and not true to scale.

DETAILED DESCRIPTION

Figure 1:
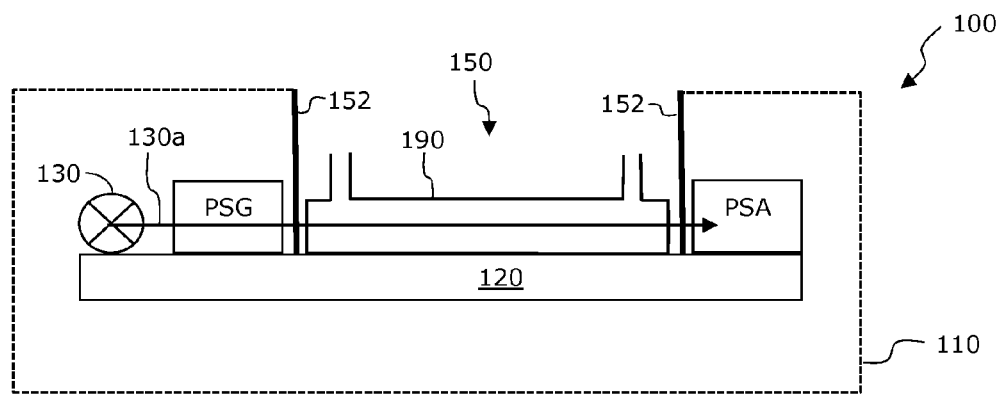
FIG. 1 shows an optical measuring system for optical polarization measurements, in which the optical components light source, PSG and PSA and the sample to be measured are arranged directly at a mechanical support structure.

It is pointed out that in the following detailed description features and/or components of different forms of embodiments which are equivalent or at least functionally equivalent with the corresponding features and/or components of another form of embodiment are given the same reference number or a reference number that only differs in the initial numeral from the reference number of the equivalent or at least functionally equivalent features and/or components. In order to avoid unnecessary repetitions features and/or components which have already been explained by way of a previously described form of embodiment are no longer explained in detail at a later point.

It is further pointed out that the following described forms of embodiment only represent a limited selection of possible embodiment variants of the invention. More particularly, it is possible to combine the features of individual forms of embodiment with each other in a suitable manner so that for a person skilled in the art with the embodiment variants explicitly set out here, a number of different forms of embodiment can be seen as being evidently disclosed.

In addition it is pointed out that space-related terms such as "at the front" and "at the back", "top" and "bottom", "left" and "right" etc. are used in order to describe the relationship of one element to another element or other elements as shown in the Figures. Accordingly, the space-related terms can apply to alignments that differ from the alignments shown in the Figures. However, it is taken for granted that for the sake of simplicity of the description all such space-related terms related to the alignments shown in the drawings and are not necessarily restrictive as the device in accordance with one form of embodiment of the invention can, when being in use, assume alignments that can differ from those shown in thee drawings.

FIG. 1 shows an optical measuring system 100 for optical polarization measurements. The optical measuring system 100, which is also referred to as a polarimeter, comprises a housing 110 in which there is a mechanical support structure 120. The mechanical support structure 120 constitutes the chassis of the polarimeter 100 and is also referred to in this document as an optical bank or integrated optical bank.

At an upper side of the optical bank 120 along an analysis beam path 130a (in FIG. 1 from left to right) there are arranged in sequence: (a) a light source 130, (b) a polarization state generator PSG, (c) a sample holder 150, and (d) a polarization state analyzer PSA. The light source 130 which can, for example, be a semiconductor laser, emits the measuring light 130a and supplies it to the analysis beam path 130a. In a known manner the polarization state generator PSG ensures that the measuring light 130a emitted from the light source 130 is polarized. The polarization state generator PSG can of course also polarize the measuring light 130a in another way. For example, the measuring light 130a leaving the polarization state generator PSG can be circularly polarized.

The optically active or optical polarization sample to be measured is arranged in the sample holder 150. In accordance with the example of embodiment shown here, the sample to be measured is a fluid sample which is located in a cuvette 190, here a so-called throughflow cuvette 190. The cuvette 190 is located on the optical bank 120 and is detachably fastened to a sample chamber enclosure 152 by means of holders which are not shown.

On passing through the sample in the cuvette 190 the polarization state of the measuring light is changed, whereby this change is dependent on the properties of the sample. The measuring light 130 which leaves the sample then impinges on the polarization state analyzer PSA, which measures the polarization state and thereby also the change in the polarization state compared with the measuring light 130a which left the polarization state generator PSG. By means of a data processing unit (not shown) downstream of the polarization state analyzer PSA the corresponding measurements are analyzed. In connection with this it is pointed out that in addition to a purely optical element which ensures that only light with a certain polarization is allowed through, the polarization state analyzer PSA can have a detector, which in the simplest case only records the intensity of the measuring light 130a which is let through by the purely optical element and hits the detector.

The optical measuring system 100 designed as a polarimeter can use as the polarization state generator PSG and/or the polarization state analyzer PSA mechanically movable prisms or Faraday modulators in combination with suitable light detectors. For the actual measurement of optical polarization properties various analysis methods can be used, e.g. by seeking intensity minima or intensity maxima and/or through compensation of an optical polarization rotation by means of the sample to be measured.

In accordance with the example of embodiment shown here the polarization state generator PSG and the polarization state analyzer PSA each have a pole filter whereby one of the two pole filters can be rotated by a motor. This rotation is measured with an encoder. From this the rotation of the polarization axis caused by the sample is determined. This measuring principle may have the advantage that it is very compact and produces little waste heat and is therefore well suited for combination with the integrated optical bank 120. This applies in particular to forms of embodiment with a temperature-controlled optical bank, which will be described below with respect to the FIGS. 3 to 6.

It is pointed out that the optical measuring system 100 described here differs from known polarimeters in particular in that the optical components light source 130, polarization state generator PSG and polarization state analyzer PSA are attached directly to the optical bank 120. The cuvette 190 containing the sample to be measured is also directly situated on the optical bank 120. Mechanical stand structures which in known polarimeters ensure spacing of the optical components from support structure are deliberately dispensed with here.

As can be seen from FIG. 1, the housing 110 together with the sample chamber enclosure 152 forms a spatial structure which on the one hand encloses all the optical components of the optical measuring system 100 and thereby protects them from harmful external influences, and on the other hand allows for a free access to the sample holder 150 from outside. In this way the cuvette 190 can be easily removed by a user from the optical measuring system 100 and replaced with a new cuvette 190 with a new fluid sample to be measured.

In order not to unnecessarily attenuate the measuring light 130a, the sample chamber enclosure 152 comprises optical windows, which are not shown, by means of which the measuring light 130 can pass without a larger attenuation.

Expressed in a descriptive manner, in the optical measuring system 100 the upper side of the optical bank 120 is a cuvette holder. In this way the cuvette is located directly on the optical bank 120 on which the other components of the optical measuring system 100 determining the accuracy of measurement are also directly mounted. This results in a particularly compact, stable construction. In the cuvette holder there are also not necessary openings which would have to be sealed. For example, in order to prevent contamination by an undesirable leakage of sample fluid, it is only necessary that the sample chamber enclosure 152 is sealed by suitable sealing element, not shown in FIG. 1, against the upper side of the optical bank 120.

Figure 2:
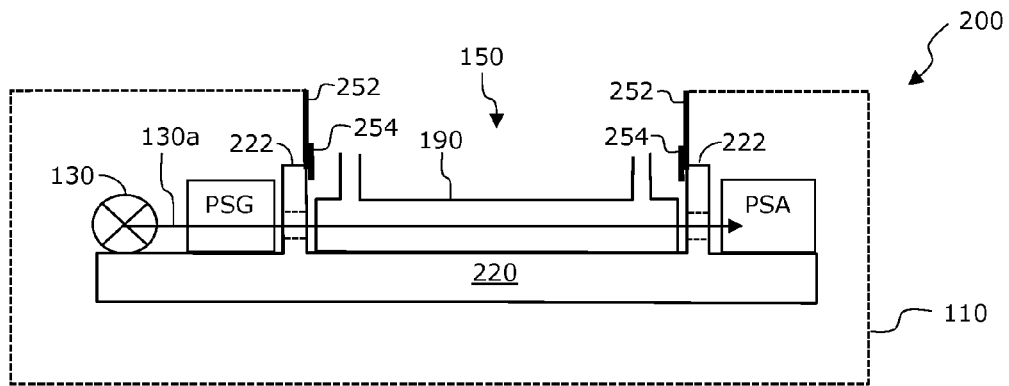
FIG. 2 shows an optical measuring system in which a sample holder is realized by means of a recess in the mechanical support structure.

FIG. 2 shows an optical measuring system 200, in which the optical bank, which is now provided with the reference number 220, is designed so that a recess is protected in which the cuvette 190 lies. As can be seen from FIG. 2, this recess is located between two projections 222, which extend upwards from the upper side of the optical bank 220. The projections 222 of the optical bank 220 thereby partially assume the task of the sample chamber enclosure 252 or extend the sample chamber enclosure 252 downwardly which is formed by the housing 110 or which is attached to the housing 110. Seals 254 between the sample chamber enclosure 252 and the relevant projection 222 ensure that the interior of the optical measuring system 200 is sealed off from the sample area. Accidentally spilled sample fluid can collect in the recess and can be easily wiped away from there. A contamination of the interior of the optical measuring system 200 by means of leaking sample fluids is therefore not to be feared.

As the spilled sample fluid will collect on the base of the sample chamber 150, no great demands are made with respect to the seals 254. They must only prevent laterally splashed sample fluids entering into the interior of the optical measuring system 200 and therefore ensure that sample fluid splashed against the sample chamber enclosure 252 provided by the housing 110 flows towards the bottom. It is therefore entirely sufficient to design the two seals 254 by way of one overlap each, so that fluid flowing downwards at the sample chamber enclosure 252 drips into the lower section of the sample chamber 150. In some circumstances the sample chamber enclosure 252 connected with the housing 110 can even be completely omitted if the projections 222 of the optical bank 220 are taken to as far as the upper side of the housing.

In order that the measuring light 130, as shown in FIG. 2, can pass through the two projections, holes are formed within these projections 222 which holes are indicated by the broken lines. These openings can of course be provided with optically transparent but otherwise closed windows, so that there is still a good seal between the sample chamber 150 and the inside of the optical measuring system 200.

Figure 3:
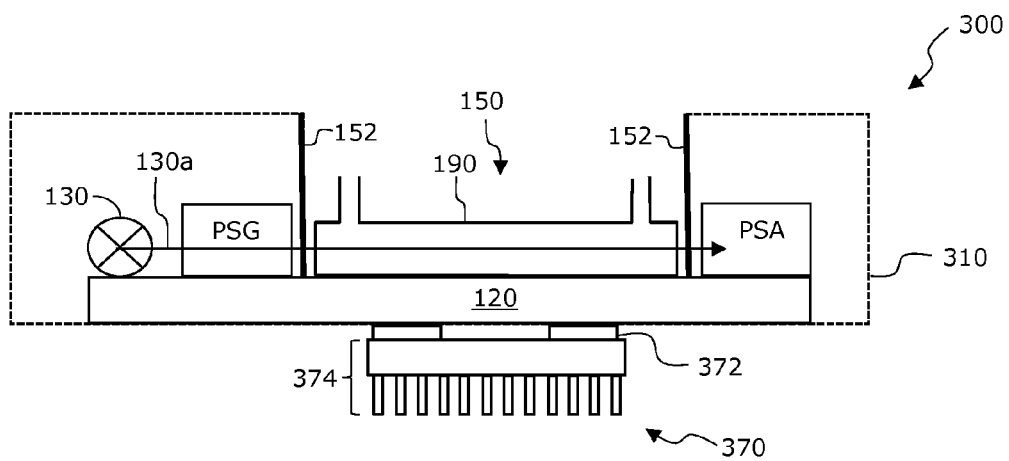
FIG. 3 shows an optical measuring system with a temperature control device, which is applied at the underside of the mechanical support structure.

FIG. 3 shows an optical measuring system 300, which in comparison with the optical measuring system 100 also comprises a temperature control device 370. The temperature control device 370, which comprises at least one thermoelectric element 372 and a cooling element 374, is attached to the underside of the mechanical support structure 120 or the optical bank 120. The temperature control device 370 can be attached by means of a thermally conductive adhesive, for example. The thermoelectric elements 372 can be Peltier elements for example.

It is pointed out that in the example of embodiment described here, by contrast to known polarimeters, which allow the temperature of a sample to be measured to be controlled, the sample is as far as possible not directly temperature controlled, but indirectly via thermal conduction by means of the optical bank 120. By means of this type of temperature control of the sample to be measured the structure of the entire optical measuring system 300 is simplified.

In order to guarantee a good temperature control of the sample to be measured, the optical bank 120 and the cuvette 190 should be designed in such a manner that there is a good thermal contact between them. As stated above, the thermoelectric elements 372 temperature control the entire optical bank 120 and through the entire optical bank 120 also the cuvette 190 and the sample fluid in the cuvette. As the polarization state generator PSG and the polarization state analyzer PSA are mounted directly on the optical bank 120, with the temperature controlling of the cuvette 190 the optical components PSG and PSA are also temperature controlled.

In connection with this it seems surprising that this design does not necessarily result in considerable measuring errors caused by this type of temperature control. If by means of a suitable temperature control temperature deviations are compensated, then changing heat quantities are pumped by means of the thermoelectric elements 372 and temperature gradients are formed in the optical bank 120. By means of the resulting thermal expansion stresses and torsions occur in the optical banks 120 which lead to measuring deviations. However, these effects are clearly dependent on the temperature of the optical bank 120. Thus, if the sample is to be measured at a predetermined temperature, this temperature must first of all be set and measuring is only carried out when the sample temperature has become stable. However, then the temperature of the optical bank 120 has necessarily stabilized so that the dynamic stresses disappear and a state of torsion is set which is determined by the static temperature of the optical bank 120. In the case of a suitable design of the contact surface of the cuvette 190 and the contact surface of the optical bank 120, the remaining temperature difference between the sample and optical bank 120 will be small, so that it can in good approximation be assumed that the measuring temperature clearly and reproducibly determines the state of torsion of the optical bank 120 and thereby the measuring deviations.

With the polarimeter 300 described here, a reference measurement can be carried out in a known manner with a cuvette that is empty or filled with an optically inactive solvent and the result being subtracted from the actual optical polarization measurements of a sample. This procedure, known as zeroing, is for compensating both static torsions and also measuring errors caused by double refraction in, for example, the cuvette end glass. Therefore, the above-described reproducible measuring deviations are reliably eliminated in normal zeroing.

Expressed descriptively, there may be measuring advantages resulting from the temperature control of the entire optical bank 120. If the components determining the accuracy of the optical measuring system 300, such as the polarization state generator PSG and polarization state analyzer PSA are mounted on the optical bank 120 with good thermal contact, they are also reproducibly temperature controlled to the measuring temperature. In this way their temperature dependencies can also be taken into account in the zeroing of the optical measuring system 300. By means of a definitive temperature control of all accuracy-determining components a particularly good drift behavior of the optical measuring system 300 can be achieved.

As can be seen in FIG. 3, the optical measuring system 300 further differs from the optical measuring system 100 in that the underside of the housing 310 coincides with the underside of the mechanical support structure or the optical bank 120. In other words, the underside of the optical bank 120 forms a part of the housing 310. This means that the temperature control device 370 is located outside of the housing 310 of the optical measuring system 300. This may have the advantage that the dissipation of heat from the cooling element 374 to the environment affects neither the interior of the optical measuring system 300 nor the sample chamber 150 of the optical measuring system 300. This allows for a particularly precise temperature control of the sample to be measured. The underside of the optical bank 120, which is not covered by Peltier elements 372, can be thermally isolated from the environment.

Figure 4:
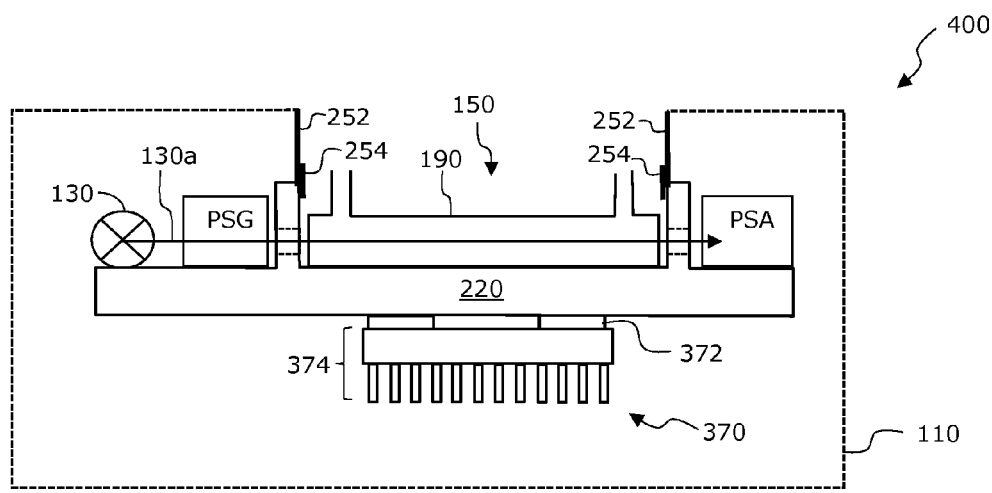
FIG. 4 shows an optical measuring system with a housing which surrounds the temperature control device.

FIG. 4 shows an optical measuring system 400 with a housing 110 which surrounds the temperature control device 370. Apart from the temperature control device 370 the optical measuring system 400 corresponds to the optical measuring system 200 shown in FIG. 2.

The temperature control device 370 can consist of several thermoelectric elements. These can, if necessary, be fitted with separate cooling elements 374. The thermoelectric elements 372 can be either affixed to the optical bank 220 and the cooling element with permanently elastic thermosadhesives or screw-fixed between the optical bank 120 and the cooling elements 374. This fastening is preferably in the form of liner screwing along the optical axis of the analysis beam 130a.

Figure 5:
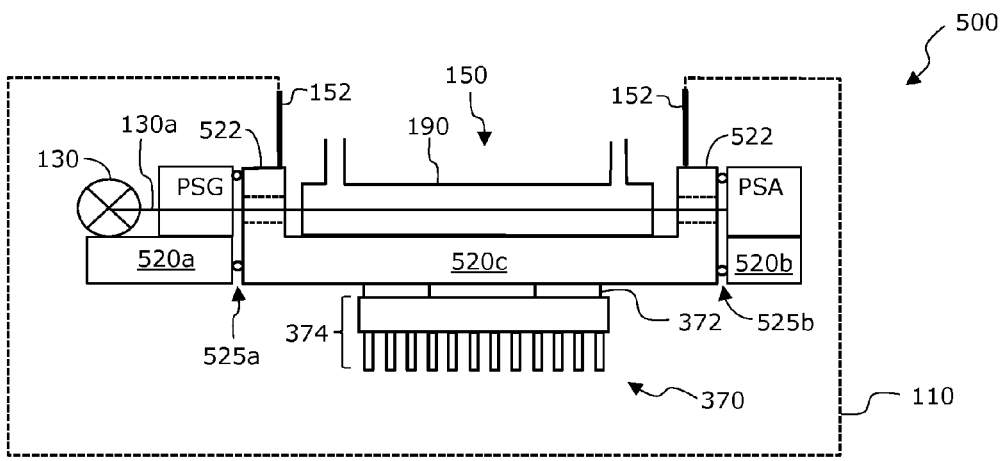
FIG. 5 shows an optical measuring system in which the mechanical support structure comprises several support elements which are arranged at a distance from one another in parallel to a direction of an optical axis of the measuring system.

FIG. 5 shows an optical measuring system 500 in accordance with a further example of embodiment of the invention. In contrast to the optical measuring system 400 shown in FIG. 4, in the optical measuring system 500 the mechanical support structure is divided into a total of three segments. The mechanical support structure is therefore designed in multiple parts and has a first support element 520a, a second support element 520b, and a third support element 520c. The three support elements 520a, 520b, 520c are arranged in a row which is orientated in parallel to the beam path of the measuring light 130a. The first support element 520a and the third support element 520c are connected to each other by means of a first coupling structure 525a. The third support element 520c and the second support element 520b are connected to each other by means of a second coupling structure 525b.

Located on the first support element 520a, directly attached to the surface of the first support element 520a, are the light source 130 and the polarization state generator PSG. On the second support element 520b, also directly connected to the surface, is the polarization state analyzer PSA. On the third support element 520c, directly attached to the surface, is the sample holder 150 respectively the cuvette 190 contained therein. As can be seen in FIG. 5, attached to the underside of the third support element 520c is the temperature control device 370.

The gaps between two adjoining support elements constitute a major barrier for the heat flow within the mechanical support structure. The two coupling structures 525a, 525b exhibit a much poorer thermal conduction as compared to a solid element. Thus, the optical components of the optical measuring system 500, i.e. (a) the light source 130 and the polarization state generator PSG arranged on the first support element 520a and (b) the polarization state analyzer PSA arranged on the second support element 520b are largely thermally decoupled from the third support element 520c and thereby from the temperature control device 370. As a result, temperature controlling of the sample does not automatically lead to a temperature change of the central optical components PSG and PSA.

As has already been described above, the coupling mechanism can also ensure that mechanical stresses, occurring in the third support element 520c for example (and caused by the temperature control device 370 for example,) are not transmitted to the other support elements 520a and 520b. As such transmitted mechanical stresses can also lead to undesirable torsions between the polarization state generator PSG and the polarization state analyzer PSA, by means of a certain mechanical decoupling between adjacent support elements the measuring accuracy of the optical measuring system 500 can be improved accordingly.

The two coupling structures 525a and 525b was well as any further mechanical couplings between the cooling element 374, the thermoelectric elements 372 and the third support element 520c, can be designed in such a way that torsion caused by the temperature control device 370 is minimally transmitted to the two support elements 520a and 520b. Suitable couplings can be realized, for example, by means of adhesion, a screw connection only along a middle axis or an assembly by means of a so called rod pressure.

Figure 6:
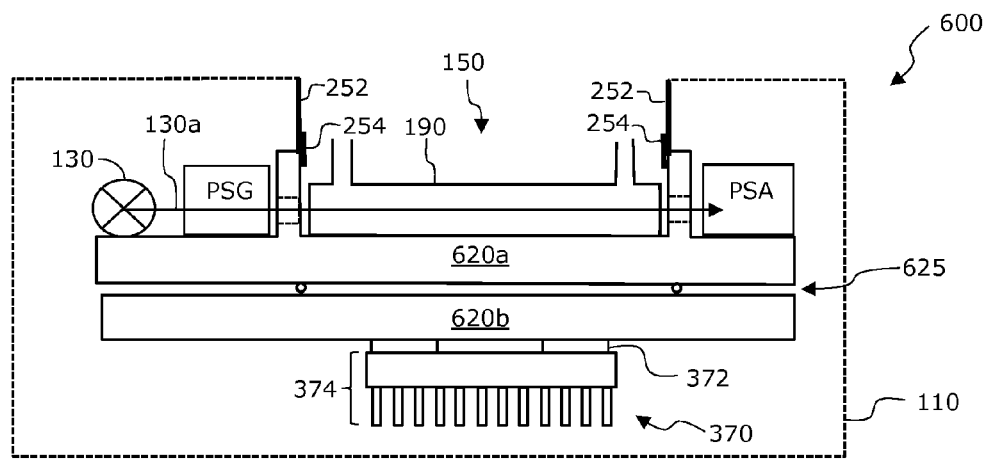
FIG. 6 shows an optical measuring system in which the mechanical support structure comprises several support elements which are spaced apart from one another perpendicularly to the direction of the optical axis of the measuring system.

FIG. 6 shows an optical measuring system 600, in which the mechanical support structure comprises two support elements 620a and 620b at a distance from one another perpendicularly to the direction of the optical axis 130a of the measuring system 600. Descriptively expressed, the first support element 620a is located above the second support element 620b.

In a gap between the two support elements 620a and 620b there is situated a coupling mechanism 625. The coupling mechanism 625 is designed in such a way that mechanical stresses present in the in the second support element 620b, and caused, for example, by the temperature control device 370, are not transmitted to the first support element 620a and thereby to the optical components of the optical measuring system 600.

The coupling mechanism 625 also constitutes a barrier for a heat transfer between the two support elements 620a and 620b. In order to nevertheless allow a temperature control of the first support element 620a and thereby of the cuvette 190 located on the first support element 620a, the properties of the surface of the two support elements 620a and 620b facing each other are such that a heat transfer is possible between the two support elements 620a and 620b by means of heat radiation. The thermal coupling of the two support elements 620a and 620b is improved by means of the comparatively large surfaces of the two support elements 620a and 620b that face each other. In order to improve the thermal coupling, between the support element 620a and the support element 620b there can be provided means for a thermo-transfer through fluids or a thermo-pad. In this way, also with the optical measuring system 600, by means of a suitable operation of the temperature control device 370, the fluid sample contained in the cuvette 190 can be indirectly temperature controlled via the second support element 620b and the first support element 620a. At the same time it is reliably prevented that mechanical stresses are transferred from the temperature control device 370 to the first support element 620a and thereby to the components of the optical measuring system 600 located on the first support element 620a. In this way, in spite of the very simple and compact design of the optical measuring system 600 a high degree of measuring accuracy can be guaranteed.

Figure 7A:
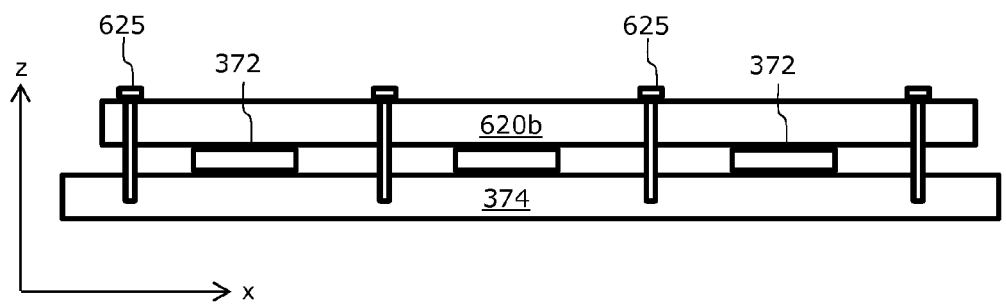
FIGS. 7a and 7b each show an enlarged view of an arrangement by means of which both the coupling mechanism shown in FIG. 6 and a good thermal coupling of the thermoelectric elements to the second (lower) support element can be realized.
Figure 7B:
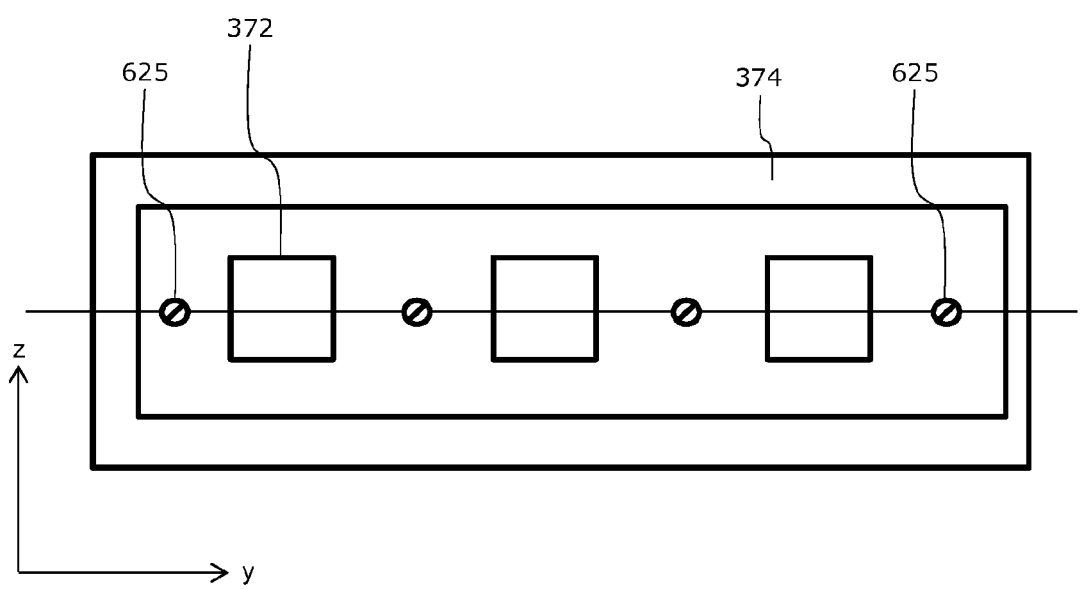

FIGS. 7a and 7b show a preferred form of embodiment of an arrangement, by means of which both the coupling mechanism 625 of the optical measuring system 600 shown in FIG. 6 and also good thermal coupling of the thermoelectric elements 372 to the second (lower) support element 620b can be realized. FIG. 7a shows a side view (like FIG. 6) respectively a section in an xz plane. FIG. 7b is a top view along the z-direction, so that arrangement is shown in the yz plane of a Cartesian xyz coordinate system.

In accordance with the example of embodiment shown here, the coupling mechanism is realized by means of four screws 625 which clamp the thermoelectric elements 372 between the cooling element 374 and the second (lower) support element 620b. The screws 625 are arranged precisely along the optical axis of the polarimeter. Onto this arrangement shown in FIGS. 7a and 7b, the optical bank 620a, which is not shown here, is mounted. In the direction of the optical axis the optical bank 620a has a recess for accommodating the screw head of the coupling elements 625 in the form of screws.

The coupling is realized along a line parallel to the optical axis. If several thermoelectric elements 372 are used, these are preferably placed in a row along this line.

It is pointed out that the arrangement described here can also be used for the thermal connection of the temperature control device 370 to the optical banks 120, 220 and 520c, which are shown in the FIGS. 3, 4 and 5.

Figure 8A:
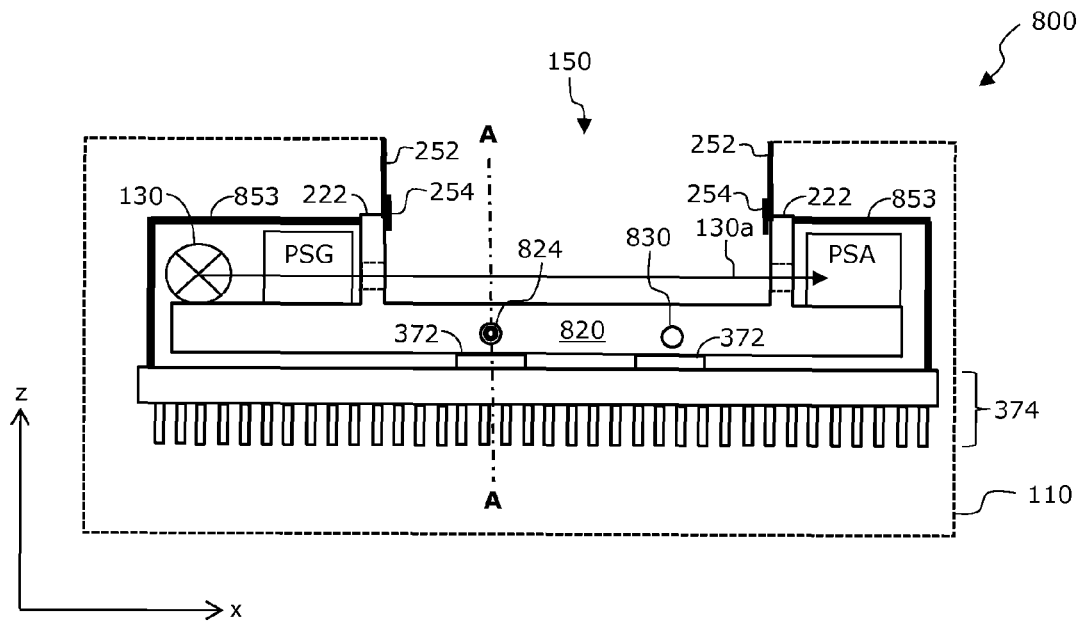
FIG. 8a shows an optical system in which the mechanical support structure in a plane parallel to the used temperature-control elements and perpendicular to the optical axis comprises recesses for holding elements.

FIG. 8a shows an optical measuring system 800 in accordance with a further example of embodiment. A mechanical support structure 820 of the measuring system 800 which is again designed as a polarimeter is drilled through or milled perpendicularly to the analysis beam (i.e. along a y axis of a Cartesian xyz coordinate system). The corresponding, at least one, recess 830 in the mechanical support structure 820 is located precisely above a thermoelectric element 372. Preferably, above every thermoelectric element 372 (in this case two) there is located a recess 830. The cross-section of the recess 830 can be arbitrary. However, preferably for manufacturing reasons the recess 830 is a cylindrical hole.

Figure 8B:
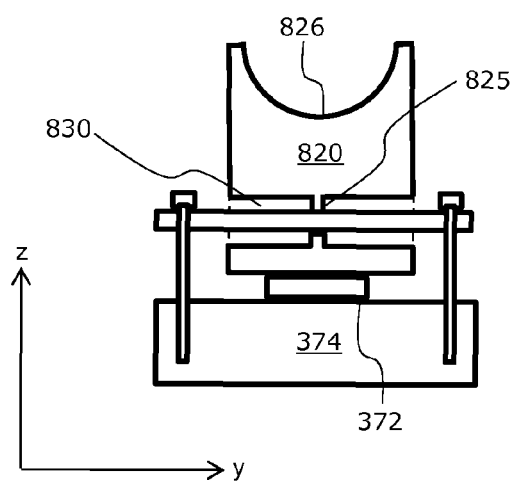
FIG. 8b shows a cross-section along points A-A of the arrangement 800 from FIG. 8a perpendicularly to the optical axis.

Precisely above the middle of the thermoelectric element 372 there is a constriction in the recess 830. In FIG. 8b, which in the yz plane of a Cartesian xyz coordinate system shows a cross section inter alia of the mechanical support structure 820, this constriction is designated with reference number 825.

As can be seen from FIG. 8b, in accordance with the example of embodiment shown here, the mechanical support structure 820 is convex in shape at its upper side, which can serve as a cuvette holder 826.

For the clamped fixation of the thermoelectric elements 372 between the mechanical support structure 820 and the cooling element 374 a holding element 824 (for example a rod or bar) is passed through this recess 830 and the ends of the holding element 824 are fastened to the cooling element, e.g. by means of screws. Only at the constriction point 825 of the recess 820 the holding element 824 is in mechanical contact with the mechanical support structure 820 and only at this point it transmits forces to the mechanical support structure 820. In this way, forces can only act in the direction of the cooling element 374 (in FIG. 8b in the negative z direction) and there are no torsion components.

The type of assembly described in FIGS. 8a and 8b only produces a small thermal coupling between the cooling element 374 and the mechanical support structure 820 as there is only a small contact area between the holding element 824 and the mechanical support structure 820 and the length of the thermal path via the holding element 824 and the screws to the cooling element 374 is relatively large. Thus, in spite of its function as, among other things, a mechanical clamping means, the cooling element 374, which is connected to one side of the thermoelectric element 372, is thermally isolated from the other side of the thermoelectric element 372, which is connected to the mechanical support structure 820. Therefore, a particularly efficient temperature control by means of the thermoelectric element 372 is possible.

If several thermoelectric elements 372 arranged in a row are used, then such a rod fixation can be used above every thermoelectric element 372. Due to the small relative dimensions of the recesses 830 in relation to the entire volume respectively the entire mass of the mechanical support structure 820, a good thermal contact of the thermoelectric elements 372 with the mechanical support structure 820 can still be guaranteed.

In order to avoid problems with condensed water which can deposit at the temperature-controlled mechanical support structure 820, if the set temperature is below the dew point of the surrounding air, the entire mechanical support structure 820 can be provided with an enclosure that is impermeable to water vapor. This enclosure is shown with reference number 853 in FIG. 8a. In accordance with the example of embodiment shown here the enclosure 853 extends from the cooling element 374 to the projections 222 of the mechanical support structure 820 and thus surrounds all the moisture-sensitive components of the optical measuring system 800. For further prevention of condensation in the enclosure 853 a drying agent can be integrated.

The thermal contact between the thermoelectric elements 372 and the adjoining components of the cooling element 374 and mechanical support structure 820 should be selected so that it has sufficient mechanical flexibility in order to minimize the transmission of torsion forces. In order to obtain good thermal contact, carbon films and filled silicone film, for example, can be used between the thermoelectric elements 372 and the mechanical support structure 820. The entire arrangement of the individual components of the optical measuring system can also be connected by further suitable fastening means.

REFERENCE NUMBERS

100 Optical measuring system, polarimeter
110 Housing
120 Mechanical support structure/optical bank
130 Light source
130a Measuring light/analysis beam path/optical axis
150 Sample holder
152 Sample chamber enclosure
190 Cuvette
PSG Polarization state generator
PSA Polarization state analyzer
200 Optical measuring system, polarimeter
220 Mechanical support structure/optical bank
222 Projection
252 Sample chamber enclosure
254 Seal
300 Optical measuring system, polarimeter
310 Housing
370 Temperature control device
372 Thermoelectric elements/Peltier elements
374 Cooling element
400 Optical measuring system, polarimeter
500 Optical measuring system, polarimeter
520a First support element
520b Second support element
520b Third support element
525a First coupling structure
525b Second coupling structure
600 Optical measuring system, polarimeter
620a First support element
620b Second support element
625 Coupling mechanism
800 Optical measuring system, polarimeter
820 Mechanical support structure/optical bank
824 Holding element/rod
825 Constriction point
826 Cuvette holder
830 Recess
852 Sample chamber enclosure
853 Enclosure

The invention claimed is:

1. Optical measuring system for measuring optical polarization properties of a sample, the optical measuring system, comprising:
    a light source, adapted to emit measuring light along an optical axis of an analysis beam path of the optical measuring system;
    a polarization state generator which is arranged downstream with respect to the light source in the analysis beam path and configured to provide the measuring light with a defined polarization state;
    a sample holder, which is arranged downstream with respect to the polarization state generator in the analysis beam path and which is designed to accommodate the sample to be measured;
    a polarization state analyzer, which is arranged downstream with respect to the sample holder in the analysis beam path and which is configured to measure the polarization state of the measuring light after passing through the sample;
    a mechanical support structure, at which at least the polarization state generator, the sample holder and the polarization state analyzer are directly attached, wherein the mechanical support structure consists of a solid component; and a temperature control device attached to the mechanical support structure in such a manner that a sample located in the sample holder can be indirectly temperature-controlled by the mechanical support structure.

2. Optical measuring system as set forth in claim 1, wherein the temperature control device is attached to a first side of the mechanical support structure, and the sample holder is attached to a second side of the mechanical support structure, wherein the first side is opposite the second side.

3. Optical measuring system as set forth in claim 1, wherein the temperature control device is a thermoelectric temperature control device which comprises one thermoelectric element or a plurality of thermoelectric elements.

4. Optical measuring system as set forth in claim 3, wherein the at least one thermoelectric element is clamped between a cooling element of the thermoelectric temperature control device and the mechanical support structure.

5. Optical measuring system as set forth in claim 3, wherein the support structure and the at least one thermoelectric element are connected to each other in an at least approximately torsion-free manner.

6. Optical measuring system as set forth in claim 1, further comprising:
a temperature regulation circuit for a regulated temperature controlling of a sample accommodated in the sample holder.

7. Optical measuring system as set forth in claim 1, wherein the solid component is a solid metallic plate.

8. Optical measuring system as set forth in claim 1, wherein the sample holder is realized by means of a recess which is formed in the mechanical support structure.

9. Method for producing an optical measuring system, the method comprising:
providing a mechanical support structure, wherein the mechanical support structure consists of a solid component;
providing a light source, adapted to emit measuring light along an optical axis of an analysis beam path of the optical measuring system;
attaching, directly at the mechanical support structure, a polarization state generator downstream with respect to the light source in the analysis beam path, wherein the polarization state generator is configured to provide the measuring light with a defined polarization state;
attaching or forming, directly at the mechanical support structure, a sample holder downstream with respect to the polarization state generator in the analysis beam path, wherein the sample holder is designed to accommodate the sample to be measured;
attaching, directly at the mechanical support structure, a polarization state analyzer downstream with respect to the sample holder in the analysis beam path, wherein the polarization state analyzer is configured to measure the polarization state of the measuring light after passing through the sample; and
attaching a temperature control device to the mechanical support structure in such a manner that a sample being located in the sample holder can be indirectly temperature controlled by the mechanical support structure.

10. Optical measuring system as set forth in claim 1, wherein the polarization state generator is mounted on the mechanical support structure such that it is reproducibly temperature controlled to have the same temperature as the measuring temperature of the sample in the sample holder.

11. Optical measuring system as set forth in claim 1, wherein the polarization state analyzer is mounted on the mechanical support structure such that it is reproducibly temperature controlled to have the same temperature as the measuring temperature of the sample in the sample holder.

12. Optical measuring system as set forth in claim 1, wherein a side of the mechanical support structure forms a part of a housing.

13. Optical measuring system as set forth in claim 12, wherein the temperature control device is located outside the housing.

14. Optical measuring system as set forth in claim 12, wherein the sample holder is located outside the housing.

15. Optical measuring system as set forth in claim 12, wherein dissipation of heat from a cooling element affects neither an interior of the optical measuring system nor a sample chamber.

16. The method of claim 9, wherein providing a mechanical support structure includes providing a torsion free chassis.

17. The method of claim 9, wherein the steps of attaching directly at the mechanical support structure each of the polarization state generator, the sample holder, and the polarization state analyzer are performed along a single surface of the mechanical support structure.

18. The method of claim 9, wherein the temperature control device is attached along a second surface of the mechanical support structure opposed to the single surface of the mechanical support structure.

19. The method of claim 9, further comprising:
controlling a temperature of the polarization state generator by a separate temperature control.

20. The method of claim 9, further comprising:
controlling a temperature of the polarization state analyzer by a separate temperature control.

21. The method of claim 9, wherein providing a mechanical support structure includes forming a part of a housing.

22. The method of claim 9, wherein both the temperature control device and the sample holder are located outside of a housing.

23. The method as set forth in claim 9, wherein the solid component is a solid metallic plate.

24. The method as set forth in claim 9, wherein the sample holder is realized by means of a recess which is formed in the mechanical support structure.

* * * * *